(12) United States Patent
Lin et al.

(10) Patent No.: US 8,434,377 B2
(45) Date of Patent: May 7, 2013

(54) METHOD FOR MEASURING SANDABILITY OF COATING AND THE USE THEREOF

(75) Inventors: Li Lin, Wallingford, PA (US); James Lamonte Adams, Glenside, PA (US)

(73) Assignee: U.S. Coatings IP Co. LLC, Wilmington, DE (US)

( * ) Notice: Subject to any disclaimer, the term of this patent is extended or adjusted under 35 U.S.C. 154(b) by 616 days.

(21) Appl. No.: 12/663,918

(22) PCT Filed: Jun. 30, 2008

(86) PCT No.: PCT/US2008/068693
§ 371 (c)(1),
(2), (4) Date: Dec. 10, 2009

(87) PCT Pub. No.: WO2009/006357
PCT Pub. Date: Jan. 8, 2009

(65) Prior Publication Data
US 2010/0170328 A1 Jul. 8, 2010

Related U.S. Application Data

(60) Provisional application No. 60/937,821, filed on Jun. 29, 2007.

(51) Int. Cl.
*G01N 33/00* (2006.01)
*G01N 3/56* (2006.01)
(52) U.S. Cl.
USPC .................................................. 73/866; 73/7

(58) Field of Classification Search .............. 73/866, 73/7
See application file for complete search history.

(56) References Cited

U.S. PATENT DOCUMENTS

| 3,411,926 | A | * | 11/1968 | Gogek et al. | 106/208.1 |
|---|---|---|---|---|---|
| 5,209,965 | A | * | 5/1993 | Caldwell | 442/81 |
| 5,418,051 | A | * | 5/1995 | Caldwell | 442/61 |
| 5,607,998 | A | * | 3/1997 | Markusch et al. | 524/494 |
| 6,638,600 | B2 | * | 10/2003 | Gazo et al. | 428/141 |
| 6,641,463 | B1 | * | 11/2003 | Molnar | 451/41 |
| 2006/0204541 | A1 | * | 9/2006 | Zhang et al. | 424/423 |
| 2009/0162631 | A1 | * | 6/2009 | Bergandt et al. | 428/220 |
| 2010/0129592 | A1 | * | 5/2010 | Nishimura et al. | 428/91 |

FOREIGN PATENT DOCUMENTS

| EP | 1431345 A1 * | 6/2004 |
|---|---|---|
| WO | WO 9946576 A1 * | 9/1999 |

* cited by examiner

*Primary Examiner* — Hezron E Williams
*Assistant Examiner* — Rodney T Frank
(74) *Attorney, Agent, or Firm* — Sudhir G. Deshmukh; Gann G. Xu (57) ABSTRACT

The present invention is directed to a method for measuring sandability of a coating or an article. This invention is particularly directed to a method for measuring sandability of a coating or an article quantitatively by measuring weight loss of said coating or article after being sanded. This invention is also directed to a system for measuring sandability of a coating or an article using said method.

11 Claims, 10 Drawing Sheets

METHOD FOR MEASURING SANDABILITY OF COATING AND THE USE THEREOF

CROSS-REFERENCE TO RELATED APPLICATION

This application claims priority from U.S. Provisional Application Ser. No. 60/937,821 (filed Jun. 29, 2007), the disclosure of which is incorporated by reference herein for all purposes as if fully set forth.

FIELD OF INVENTION

The present invention is directed to a method for measuring sandability of a coating or an article. This invention is particularly directed to a method for measuring sandability of a coating or an article quantitatively. This invention is also directed to a system that uses said method to measure sandability of a coating or an article.

BACKGROUND OF INVENTION

It is a normal practice that after a coating composition is applied to a substrate to form a coating, the coating is then sanded to remove defects to create a desired coating surface. The desired coating surface can have desired smoothness or roughness that may be different from the original coating. Another layer or multiple layers of the same or different coating composition can be applied over the sanded coating surface to finish the substrate.

Different coating compositions can have different intrinsic properties that cause resulted coatings to have different sandability. Sandability of a coating describes how easy to sand the coating and is currently evaluated by specialists in the coating industry by sanding the coating with hand or tools. The specialists then ranking the coating or coatings, based on their judgment, as easy or difficult to sand. The evaluation is mostly subjective and varies from person to person. Since each specialist may use different tools or sanding papers for performing sanding, the evaluation is often not reproducible and inconsistent. Current, there lacks a quantitative measure for evaluating sandability of a coating.

It is therefore in need for a method for measuring sandability of a coating efficiently, quantitatively and reproducibly.

STATEMENT OF INVENTION

This invention is directed to a method for measuring sandability of a coating, said method comprising the steps of:
 a) measuring initial characteristics of a substrate coated with said coating;
 b) sanding said coating on the substrate;
 c) measuring subsequent characteristics of the substrate after the step b); and
 d) obtaining a difference between the initial and the subsequent characteristics.

This invention is directed to a method for measuring buffability of a coating comprising the steps of:
 e) measuring initial surface characteristics of the coating using a surface measuring device
 f) buffing the coating to create a buffed coating surface; and
 g) measuring subsequent surface characteristics of the buffed coating surface using the surface measuring device.

This invention is further directed to a method for comparing sandability of a plurality of coatings, said method comprising the steps of:

a) measuring individual initial characteristics of individual substrates each coated with one of said plurality of coatings;
 b) sanding the coating on each of the individual substrates;
 c) measuring subsequent characteristics of each of the individual substrates after the step c); and
 d) obtaining individual differences between the individual initial and the corresponding subsequent characteristics.

This invention is further directed to a method for comparing buffability of a plurality of coatings comprising the steps of:
 e) measuring initial surface characteristics of each of the coatings using a surface measuring device;
 f) buffing each of the coatings to create individual buffed coating surfaces; and
 g) measuring a subsequent surface characteristics of the buffed coating surfaces using the surface measuring device.

This invention is further directed to a system for measuring sandability of a coating, said system comprising:
 a) a sanding device; and
 b) an substrate measuring device.

This invention is even further directed to a method for measuring sandability of an article, said method comprising the steps of:
 a) measuring initial characteristics of the article;
 b) sanding the article;
 c) measuring subsequent characteristics of the article after the step b); and
 d) obtaining a difference between the initial and the subsequent characteristics.

This invention is even further directed to a method for measuring buffability of an article comprising the steps of:
 e) measuring initial surface characteristics of the article using a surface measuring device;
 f) buffing the article create a buffed surface; and
 g) measuring subsequent surface characteristics of the buffed coating surfaces using the surface measuring device.

BRIEF DESCRIPTION OF DRAWING

FIG. 1 shows representative flow charts of the method of this invention. (A) A representative flow chart for measuring both sandability and buffability. (B) A representative flow chart for measuring sandability. (C) A representative flow chart for measuring buffability.

FIG. 2 shows a representative example of a sanding device. (A) Representative diagram of the sanding device. (B) A photo of an example of the sanding device. (C) A perspective side view of part of the sanding device for illustrating movement control. (D) A top-down view of part of the sanding device for illustrating movement control.

FIG. 3 shows a representative example of a buffing device. (A) A representative diagram of the buffing device. (B) A photo of an example of the buffing device.

DETAILED DESCRIPTION

The features and advantages of the present invention will be more readily understood, by those of ordinary skill in the art, from reading the following detailed description. It is to be appreciated that certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both proceeded by the word "about." In this manner, slight variations above and below the stated ranges can be used to achieve substantially the same results as values within the ranges. Also, the disclosure of these ranges is intended as a continuous range including every value between the minimum and maximum values.

As used herein:

A coating means a thin layer of material covering a surface of a substrate, such as metal, wood, plastic or any other articles or materials that a coating can be applied onto. Examples of substrate include, but not limited to, automobile body, metal panels, plastic panels, wood panels, buildings, household appliances, sports equipments, or farming machines The coating can be formed by applying a thin layer of a coating composition to said substrate. A coating composition typically comprises materials that can form a thin layer under certain conditions. Examples of coating compositions include, but not limited to, acrylic coating composition that comprises acrylic materials, latex coating composition that comprises latex materials, and other coating compositions that comprises natural or manmade materials. A coating composition can further comprise pigments or dyes to produce color. A coating composition can also comprise special effect pigments such as aluminum flakes to produce special appearance effects such as sparkling. A coating composition is typically applied to a substrate by spraying, brushing, submerging or immersing, doping, or any other methods that can cause the coating composition to cover the substrate to form a coated substrate.

A coating can be a single layer formed by a single coating composition. A coating can also have multiple layers formed by one or more coating compositions. In one example, a coating is a single layer formed by a coating composition applied directly to a substrate. In another example, a coating on a substrate comprises one or more primer layers formed by one or more primer compositions, one or more basecoat layers formed by one or more basecoat compositions, and one or more topcoat layers formed by one or more topcoat compositions.

A primer refers to a coating that can be applied to a substrate to form a primer layer to prepare the substrate so additional coating layers can be applied. A primer can comprise adhesion promoter for improved adhesion between the primer layer and the substrate. A primer can also comprise one or more pigments to produce desired color. A primer can further comprise anti-corrosion additives for protecting the substrate. A primer can also be referred to as a sealer or a surfacer that can be used to seal small defects on the surface of a substrate.

A basecoat refers to a coating applied over a primer layer or directly over a substrate. A basecoat can be pigmented to produce desired color or un-pigmented. One or more layers of basecoat can be formed by one or more basecoat compositions.

A topcoat refers to a coating applied over a basecoat layer. A topcoat generally provides protection for a basecoat. A topcoat can be pigmented or un-pigmented.

A clearcoat refers to a coating generally un-pigmented.

This invention is directed to a method for measuring sandability of a coating. In one embodiment, said method comprises the following steps.

In step a) (10) (FIG. 1), initial characteristics of a substrate coated with said coating is measured. The initial characteristics can be measured with a variety of ways. Examples of such initial characteristics include, but not limited to, initial weight of the substrate coated with the coating, initial thickness of the coating on the substrate, and initial roughness or initial surface profile of the coating on the substrate.

Figure 1A:
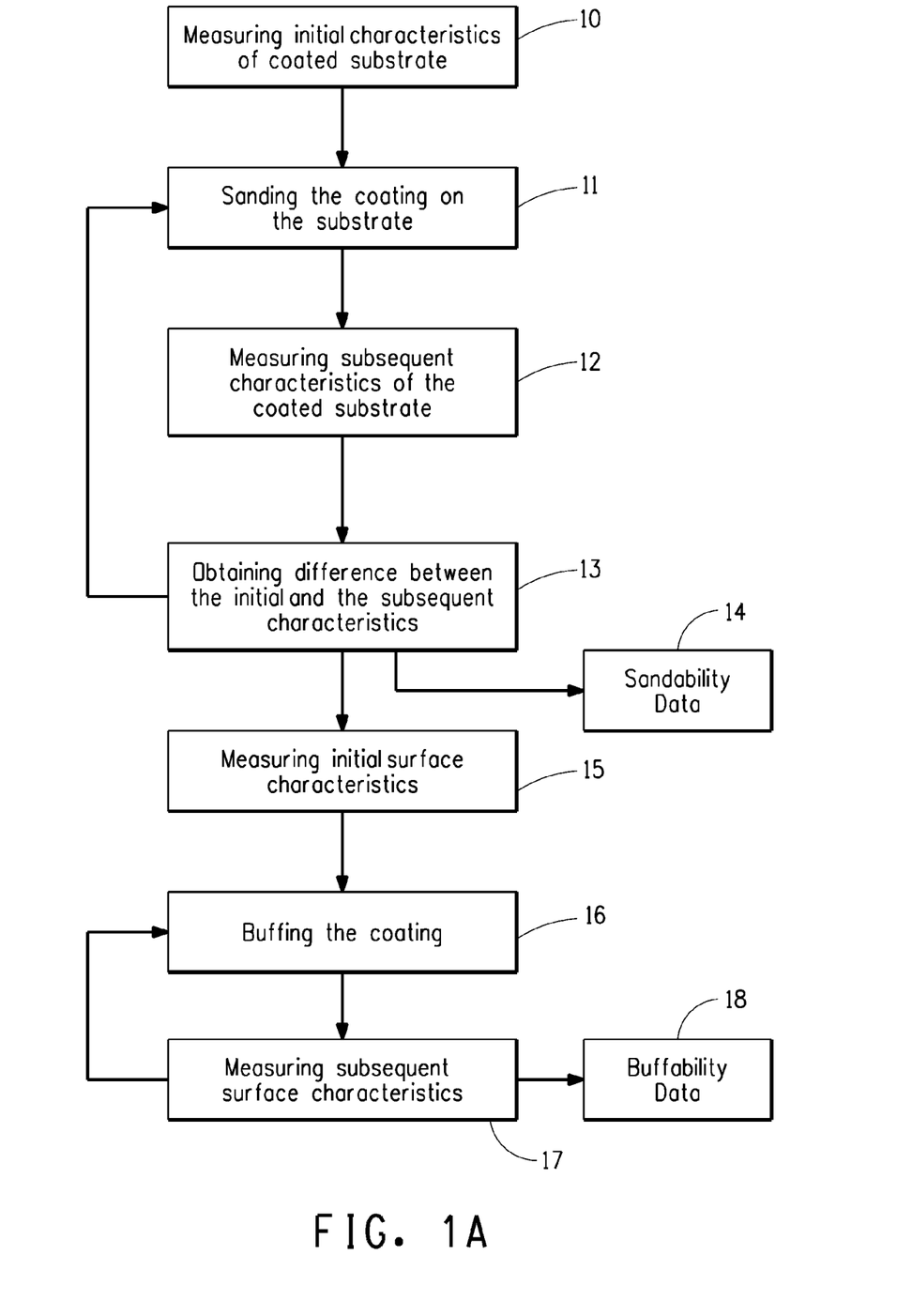
Figure 1B:
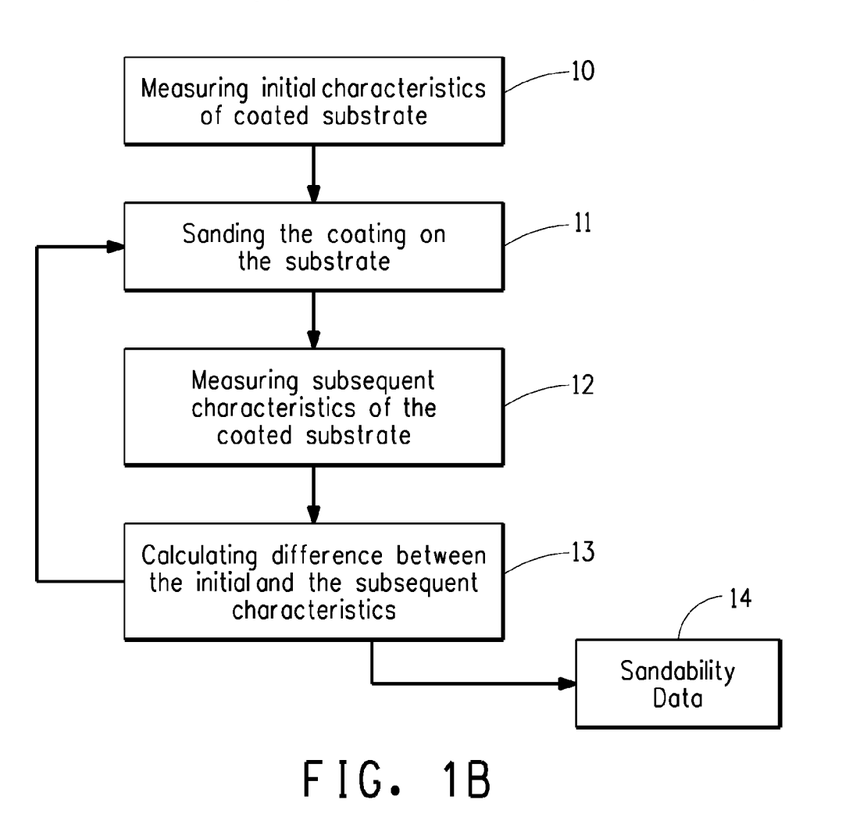
Figure 1C:
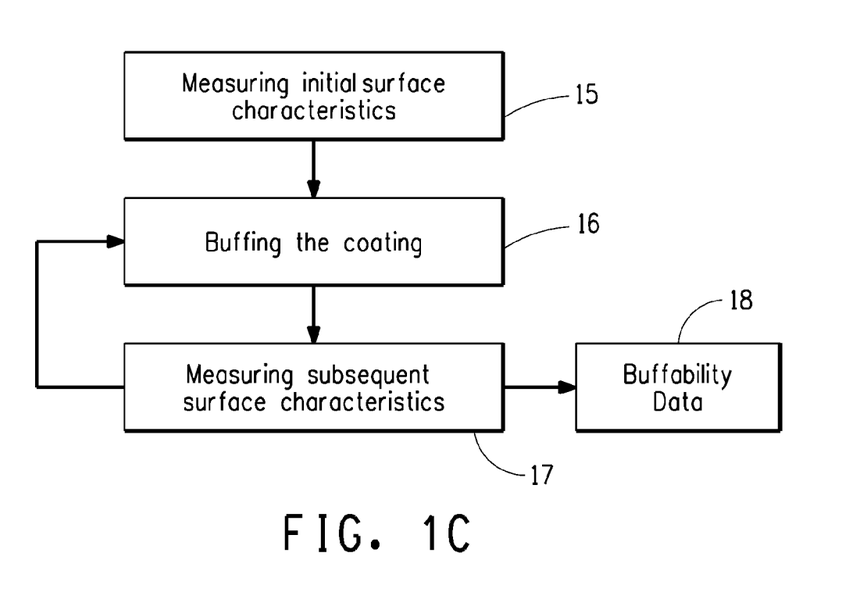

The initial weight of the substrate coated with the coating can be measured using a weight measuring device, such as a balance. It is preferred that the balance is capable of measuring weight difference in a range of from 0.0001 to 1 gram. Thickness of the coating on the substrate can be measured using a thickness gauge. Commercially available thickness gauges. Such as thickness gauge micro-TRI-glossµ from Byk-Gardner, Columbia, Md. 21046, is suitable for this invention. Roughness of the coating can be measured using a gloss meter, such as the gloss meters available from above mentioned Byk-Gardner. A coating generally reduces gloss after being sanded. Roughness can also be measured by using an imaging device. Images of the coating surface can be captured by the imaging device and enlarged for manual or automated analysis. Microstructures of the coating surface, such as microscopic lines, dots, grooves, dents that contribute to coating roughness can be analyzed and recorded. Images can be real-time image and can also be stored optically or digitally, such as stored in a photograph or in computer readable digital forms. Imaging devices, such as a still camera, a digital camera, a video camera, a microscope, or a scanner are suitable for this invention. The roughness can also be measured using a profilometer. A profilometer can measure special depth or height of microstructures of the coating surface. The measurement can be analyzed and recorded. Commercial profilometers, such as those available from Ambios Technology Inc (Santa Cruz, Calif.), Veeco (Woodbury, N.Y.), Solarius Development Inc. (Sunnyvale, Calif.), Taylor-Hobson Inc (West Chicago, Ill.) and CSM Instruments Inc. (Needham, Mass.), are suitable for this invention.

In step b) (11), the coating on the coated substrate is then sanded. The sanding can be done according to conventionally well known methods, such as using sand papers, sand blocks, or other sanding media such as sanding paste. Any conventional sanding methods are suitable for this invention.

The coating can also be sanded under controlled sanding conditions, wherein under said controlled sanding conditions, a number of factors that affect sanding, such as directions of sanding, the number of sanding strokes, forces applied to sanding (hereafter referred to as sanding force), or types of sanding media such as sanding paper, are regulated and recorded. In one example, a pre-determined number of strokes, such as 8 strokes, can be used to sand the coating in a bi-directional fashion, with a pre-determined sanding force applied.

FIG. 2 shows an example of a sanding device for sanding the coating under controlled sanding conditions. The sanding device comprises a sanding head assembly (201), a substrate holder (202) and a movement control device (203) that causes relative movement between the substrate holder and the sanding head assembly. The sanding head assembly can be attached to a frame (204) through a coupling (211). In an example, the sanding head assembly comprises an arm (210), a sanding force regulator (209), a sanding head (207), a coupling (208) that couples the arm (210) and the sanding head (207). A sanding medium (206) can be attached to sanding head (207). One example of the sanding medium is a sanding block available from Canal Rubber Supply Co., INC (New York, N.Y.). The sanding block can be affixed to the sanding head with double side adhesive paper. Sanding papers such as Imperial Wetordry 400, 600, 800, 1000, 1200, 1500 and 2000 from 3M (St. Paul, Minn.) can be used. Other commercial abrasives can also be used.

Figure 2A:
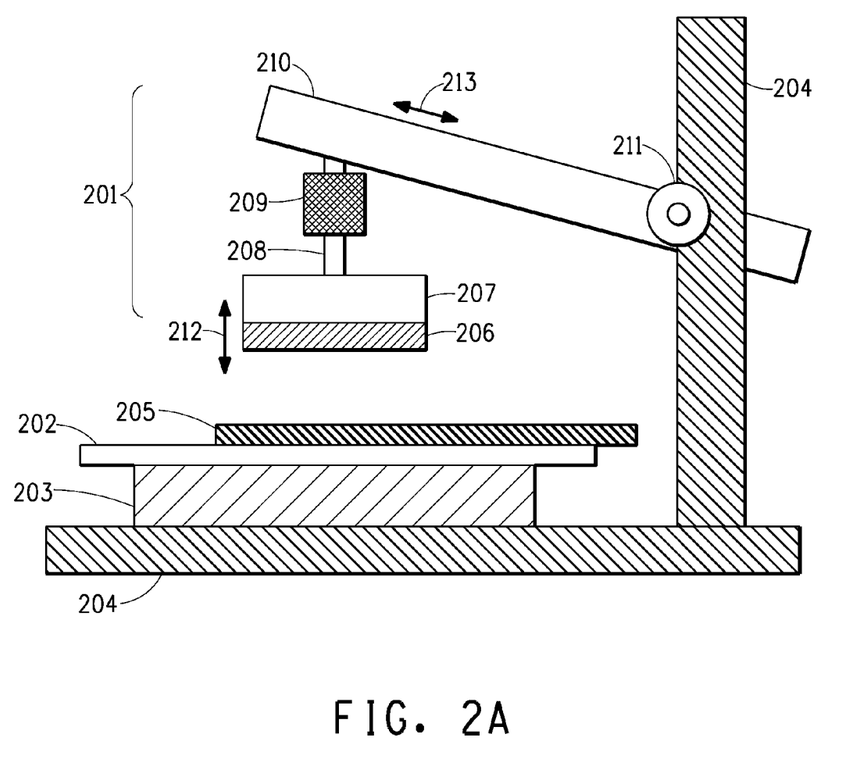

The substrate (205) can be placed on the substrate holder (202) with a coated side that is coated with the coating facing the sanding head. The substrate holder (202) can be magnified so it can hold a steel or iron substrate. The holder (202) can also comprise other means such as clips, clamps, or screws that can hold the substrate in place.

Figure 2B:
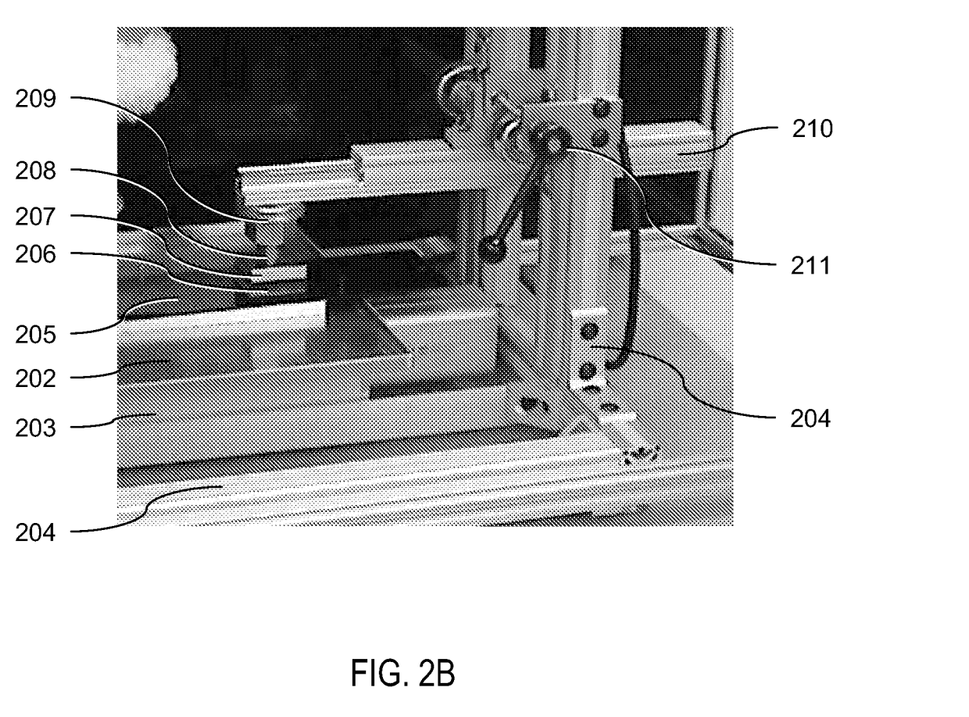
Figure 2C:
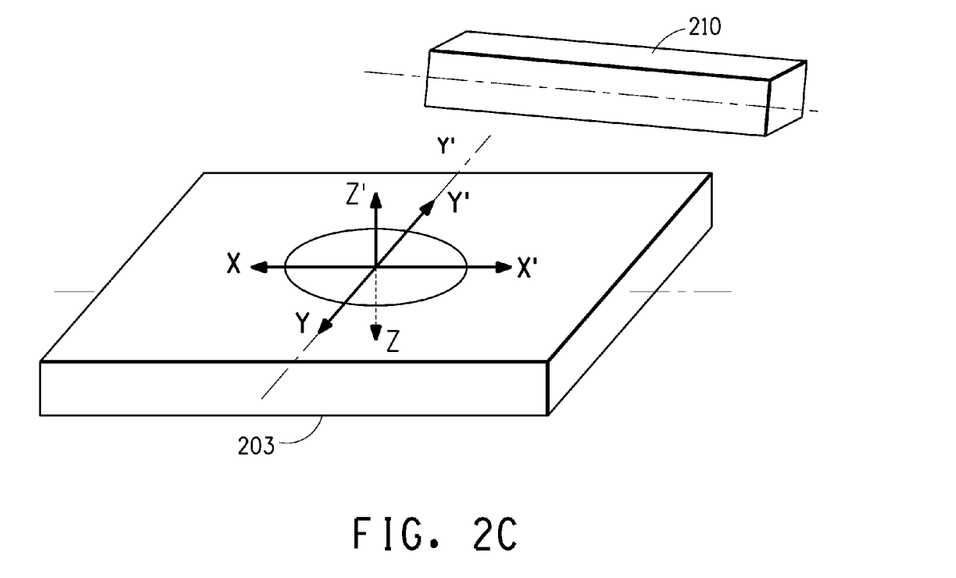
Figure 2D:
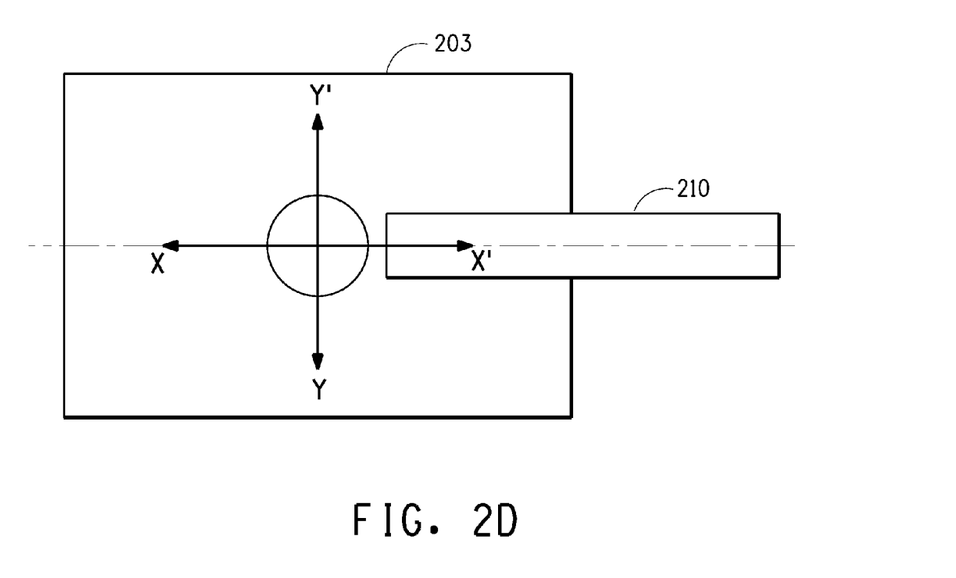

The movement control device (203) provides desired relative motion between the sanding head and the substrate. The desired relative motion can be bi-directional, such as motions in X-X' or Y-Y' direction (FIGS. 2C and D), or circular. The motions can also be partial circular oscillation or in a predetermined direction between the X-X' and Y-Y' directions. The movement control device can optionally provide vertical moment in the Z-Z' direction. The movement control device can be assembled from commercial available parts and devices. In one example the movement control device can be assembled from a linear stage from Techno-Isel (part#HL31SBM601050010) (New Hyde Park, N.Y.), a motion controller SI3540 from Applied Motion Products Inc. (Groton, Mass.) and a turntable from Vue-More Manufacturing Group (Nutley, N.J.). A photograph of an example of such sanding device is shown in FIG. 2B. In this particular example, the movement control device is placed under the substrate holder. The movement control device can also be place in other locations as long as it can cause relative motion between the sanding head and the substrate. For example, the movement control device can be placed in conjunction with the coupling (211) to cause the arm (210) to move in X-X' direction while the substrate holder remains stationary. The movement control device can also be placed on the arm (210) and coupled to the sanding head to cause the sanding head to slide while the substrate holder remains stationary. Those skilled in the art can readily make other configurations to establish relative movement between the sanding head and the substrate holder to accomplish sanding of the coating.

In step c) (12), subsequent characteristics of the substrate after sanding can be measured. Sanding process removes certain amount of coating materials from the coated substrate causing the coating to lose weight and thickness. Sanding can also cause the coating to increase roughness. Subsequent characteristics of the substrate can be measured according to the initial characteristics measured. For example, if the initial characteristics include weight, then the subsequent characteristics should also include weight. It is preferred that same device used for measuring the initial characteristics be used for measuring the corresponding subsequent characteristics.

In step d) (13), a difference between the initial and the subsequent characteristics can be obtained. If weight of the substrate is used, a weight difference, also referred to as weight loss, between the initial weight and the subsequent weight can be obtained by subtracting the subsequent weight from the initial weight. For example, if one coated panel has an initial weight of 100.00 gram and a subsequent weight of 99.78 gram after sanding, then the weight loss due to sanding is about 0.22 gram.

Thickness difference can be obtained based on initial thickness of the coating on the substrate and subsequent thickness of the coating after being sanded. A roughness difference can be obtained in a similar way. For example, a gloss difference can be obtained based on initial gloss meter readings before sanding and subsequent gloss meter reading after sanding. Roughness difference can also be obtained by comparing images of the coating surface before and after sanding. Typically, numbers or sizes of the microstructures of the coating surface can be compared. In one example, the numbers of lines and grooves per square millimeter appearing in initial and subsequent images of the coating are compared. Roughness difference can also be obtained by comparing profilometer profiles. A sanded coating surface generally has increased roughness such as increased depth or heights of the microstructures.

When necessary, the steps b) (11) through d) (13) can be repeated until desired difference between the initial and the subsequent characteristics can be achieved. For example, the weight loss needs to be exceeding a detection threshold of the balance used in order to be detected. If a first set of sanding cannot remove sufficient coating materials to cause a significant weight loss that can be detected by the balance, the coating needs to be sanded again until the weight loss can be detected by the balance. The difference between the initial and the subsequent characteristics can be part of sandability data (14) for evaluating sandability of the coating, wherein the sandability data of the coating describe sandability of said coating.

How easy a coating can be sanded is often referred to as sandability of that coating. For coatings that are difficult to sand, repeated sanding may be needed to remove significant amount of that coating so a weight loss can be obtained. Traditionally, sandability is evaluated by specialists in the coating industry by sanding the coating with hand or tools. Based on their judgment, the specialists then ranking the coating or coatings as easy or difficult to sand. The evaluation is mostly subjective and varies from person to person. Since each specialist may use different tools or sanding papers for performing sanding, the evaluation is often not reproducible and in consistent. The weight loss data generated by this method provide a quantitative measure for sandability evaluation.

It is preferred that the coating is sanded under a controlled sanding condition, such as using a certain sanding block, with a certain number of sanding strokes, with certain sanding force applied to the sanding force regulator, and with given sanding directions. Weight loss data on one or more coatings produced after sanding under the controlled sanding conditions can be directly associated to sandability of the coatings. Sandability of one or more coatings can be compared using weight loss data. For example, two coatings can be sanded under same pre-determined conditions, one coating having greater weight loss can be assigned "easy to sand" sandability, while the other coating having less weight loss can be assigned a sandability "hard to sand". Those skilled in the art can also use other descriptive terms, such as numerical or alpha numerical characters to describe sandability. One commonly used descriptive is numerical rating, such as a 1-10 rating with 1 being most difficult to sand and 10 being easiest to sand.

Method of this invention can be used for measuring and comparing sandability of various coatings. A coating can be a single layer formed by a single coating composition, such as a primer. A coating can also be of multiple layers, such as a finished automobile body that typically has at least one layer of primer, one or more layers of basecoat with pigments that produce colors, and one or more layers of clearcoat that produce desired gloss and other desired coating properties.

Sanding is usually performed to remove certain defects of a coating, such as slight variations on thickness, dripping marks, or brush stroke marks. Sanding also creates a rough surface to provide adhesion for next layer of coating. For example, a primer layer is usually sanded to even surface with certain roughness so a basecoat can be applied.

In other situations, sanded surface need to be polished by a process known as buffing to achieve desired smoothness, for example, clearcoat used for high gloss of an automobile finish. A buffing step can be used to polish the sanded coating. Buffing can also be done independently without prior sanding.

This invention is also directed to a method for measuring buffability of a coating. In one embodiment, the method of this invention comprises the following steps.

In step e) (15), initial surface characteristics of the coating can be measured using a surface measuring device. Surface characteristics of the coating surface can also be measured using a variety of other methods, for example, by visual examination by naked eyes or using optical microscope. It is preferred in this invention that the coating surface is measured using surface measurement devices. Aforementioned devices such as gloss meter, imaging device, profilometer, or a combination thereof, can be suitable for this invention.

In step f) (16), the coating can be buffed using a buffing device to create a buffed coating surface. A number of commercial buffing devises are available. For example, orbital high speed polisher available from DeWalt Hampstead, Md. 21074, can be suitable for this invention. Buffing can be done manually or automatically with electronic controls.

Figure 3A:
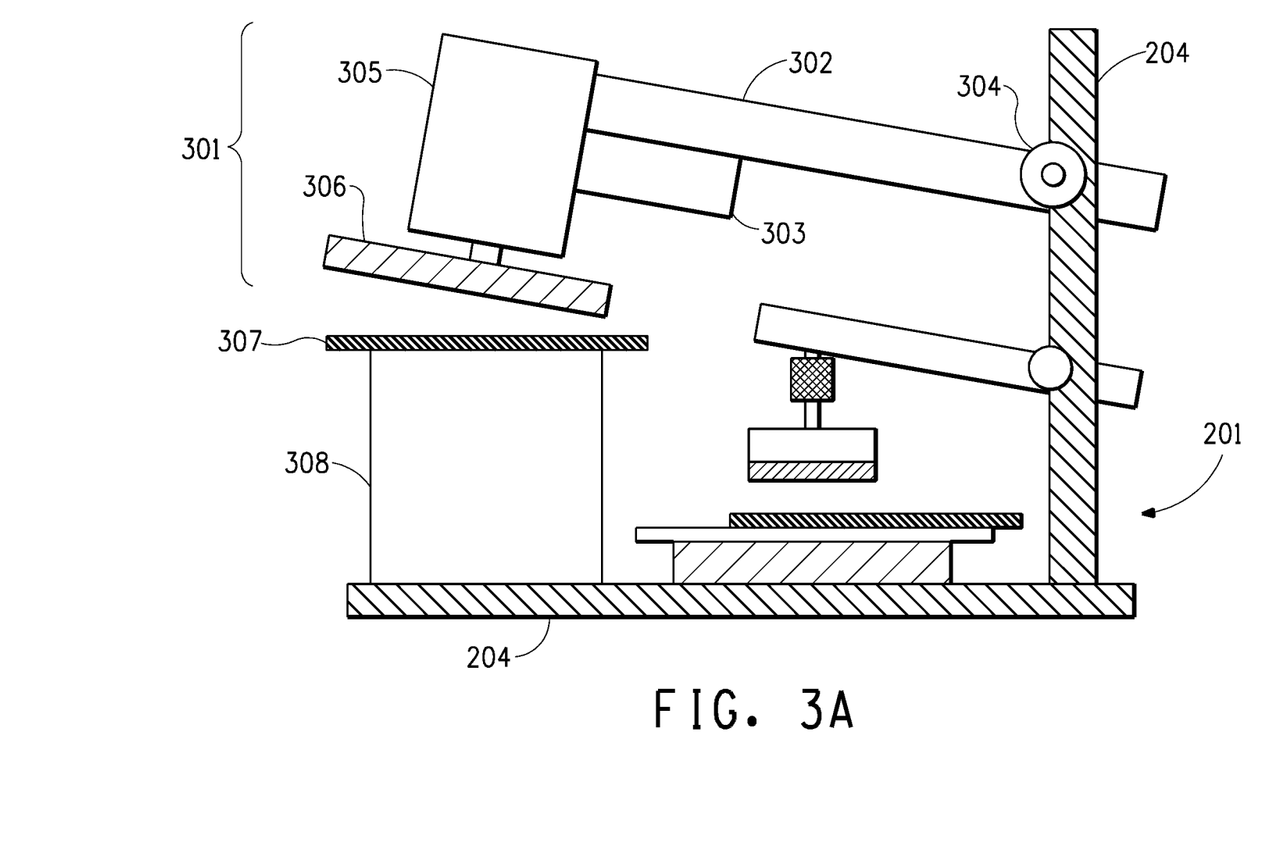
Figure 3B:
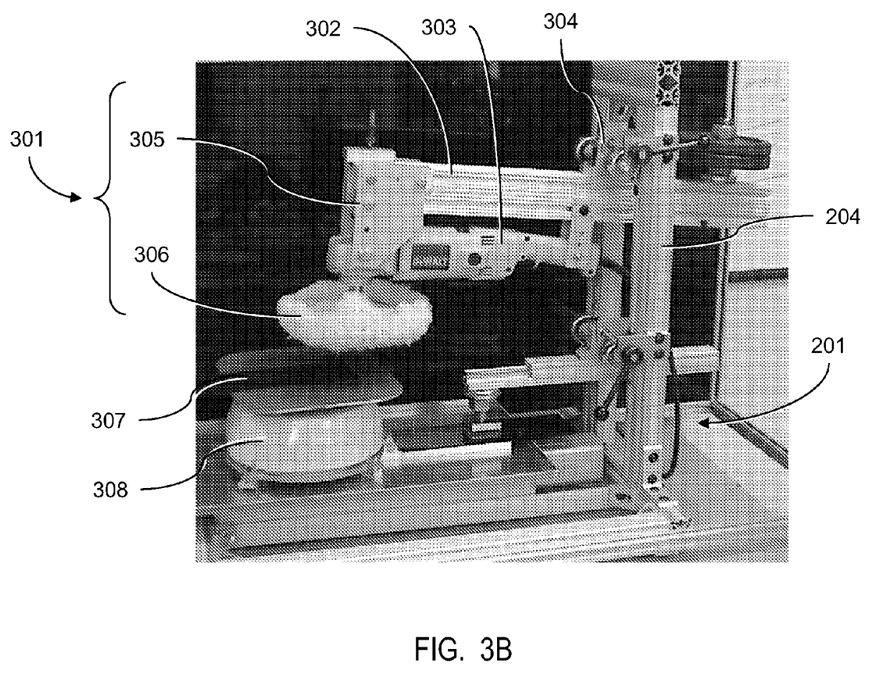

One example of a buffing device with automatic electronic control is shown in FIG. 3. A buffing head assembly (301) can comprise a buffing head (306) coupled to a power source (303) such as a DeWalt high speed polisher. The buffing head and the power source are the attached to a buffing arm (302) though one or more buffing couplings (305). The buffing arm can be affixed to the frame (204) though a frame coupling (304). A buffing pad or other buffing medium can be attached to the buffing head (306). A coating substrate (307) can be held by a buffing holder (308). An electronic controller can control buffing speed and buffing time. Such buffing controller is well known to those skilled in the art. A buffing pressure can also be applied through the buffing arm to the buffing head to modulate contact pressure between the buffing head and the substrate.

In step g) (17), surface characteristics of the coating after buffing can be measured using the surface measuring device. It is understood that corresponding measurement should be used, for example, if the initial characteristics comprise gloss meter measurement, the subsequent characteristics should also comprise gloss meter measurement. It is also preferred that the same surface measurement device is to be used for measuring the initial and the subsequent characteristics.

Surface characteristics that can be measured by an imaging device include, but not limited to, microstructures, such as microscopic lines or dents cutting into a coating surface, or dots or small areas protruding from the coating surface that contribute to roughness of the coating surface. Images of a coating surface before and after buffing can be captured using the imaging device and the images can be enlarged to show those microscopic lines, dents or other surface characteristics. Such microscopic lines or dents can be counted manually or automatically using a computer implemented method. Image analysis data, such as the number of lines or dents in a given area or linear length can be generated and compared for the coating surface before and after buffing. Buffability data that represent how easy the coating can be buffed to reduce roughness of the coating surface can be generated based on the image analysis data. Buffability of a plurality of coatings can be compared.

Another method to measure surface characteristics is to measure gloss of the surface. A sanded surface reflects lights in less unidirectional fashion due to roughness of the surface. Buffing generally reduces roughness and therefore increases unidirectional light reflection that can be measured with a gloss meter. Gloss meters available from Byk-Gardner, Columbia, Md. 21046, are suitable for this invention.

Yet another method to measure surface characteristics is to use proliformeter. A proliformeter measures not only the number of above mentioned lines, dots, or dents, but also measures depth of those lines, dots, or dents. Buffing can reduce the number of those lines. Under some situations, some of the lines are not completely buffed away, but reduced in depth. Profilometer is suitable for measuring such reduction in both the number and depth of the lines.

Buffability of a coating describes how easy to reduce surface roughness of the coating. Buffability can be determined with buffability data that can comprise parameters, such as buffing time, roughness of the coating surface, types of buffing pads, buffing rotor speeds, or buffing pressures. Roughness of the coating surface can be described by the number of lines per millimeter; gloss meter reading; or proliformeter measurement, such as depth or height of the microstructures, or the number of microstructures in a certain area. If conventional buffing media is used, the type of buffing media can also be part of the pre-determined constant conditions. Buffability of a plurality of coatings can be compared based on the buffability data.

In one example, some of the parameters, herein referred to as constant parameters, such as type of buffing pads, buffing rotor speed, or buffing pressure, can be kept constant. Other parameters, herein referred to as varying parameters, such as buffing time needed for reaching a certain gloss meter reading, can be used to compare buffability of a plurality of coatings.

In another example, buffing conditions, such as buffing time, buffing pad and buffing rotor speed, are kept constant when buffing a plurality of coatings individually. Profilometer measurements of each of the individual buffed coatings, such as height of microstructures or the number of microstructures per millimeter, can be used to compare buffability of the plurality of the coatings.

This invention is also directed to a system for measuring sandability of a coating. In one embodiment, said system comprises a sanding device and a weight measuring device. The sanding device further comprises a sanding head assembly; a substrate holder that holds a substrate coated with said coating; and a movement control device that causes relative movement between the substrate holder and the sanding head assembly. The sanding head assembly can further comprise a sanding force regulator for modulating force applied to the sanding head.

The weight measuring device can be a balance capable of measuring weight differences in a range of from 0.0001 gram to 1 gram.

The system of this invention can further comprise a buffing device and a surface measuring device.

Although a coating is specifically described, the method of this invention can also be use for measuring sandability or buffability of other articles, surfaces, or a combination thereof. For example, sandability of certain material, such as metal, plastic, or wood, can be measured by sanding samples of those materials and obtaining weight loss data. Buffability of those materials can be measured by sanding, buffing and measuring surface characteristics of samples of those materials.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Example 1

Sanding of Coatings

Four different primers were coated onto metal testing panels using conventional spray application methods. Each primer was coated onto at least 4 separate testing panels. The four primers were 3240S, 1107S 1140S and 131S available from DuPont, Wilmington, Del. The coated primers were cured for 23-25 hours at room temperature.

Each of the 4 testing panels for each primer was sanded for 16 strokes by one of the four independent operators using the sanding device shown in FIG. 2. Sanding was done in X-X' directions.

Initial weights of each of the testing panels were obtained by weighing using a balance. After the 16 stroke sanding, subsequent weights were obtained using the same balance. Weight loss for each of the testing panels after sanding was calculated as sandability data and shown in FIG. 4.

Figure 4:
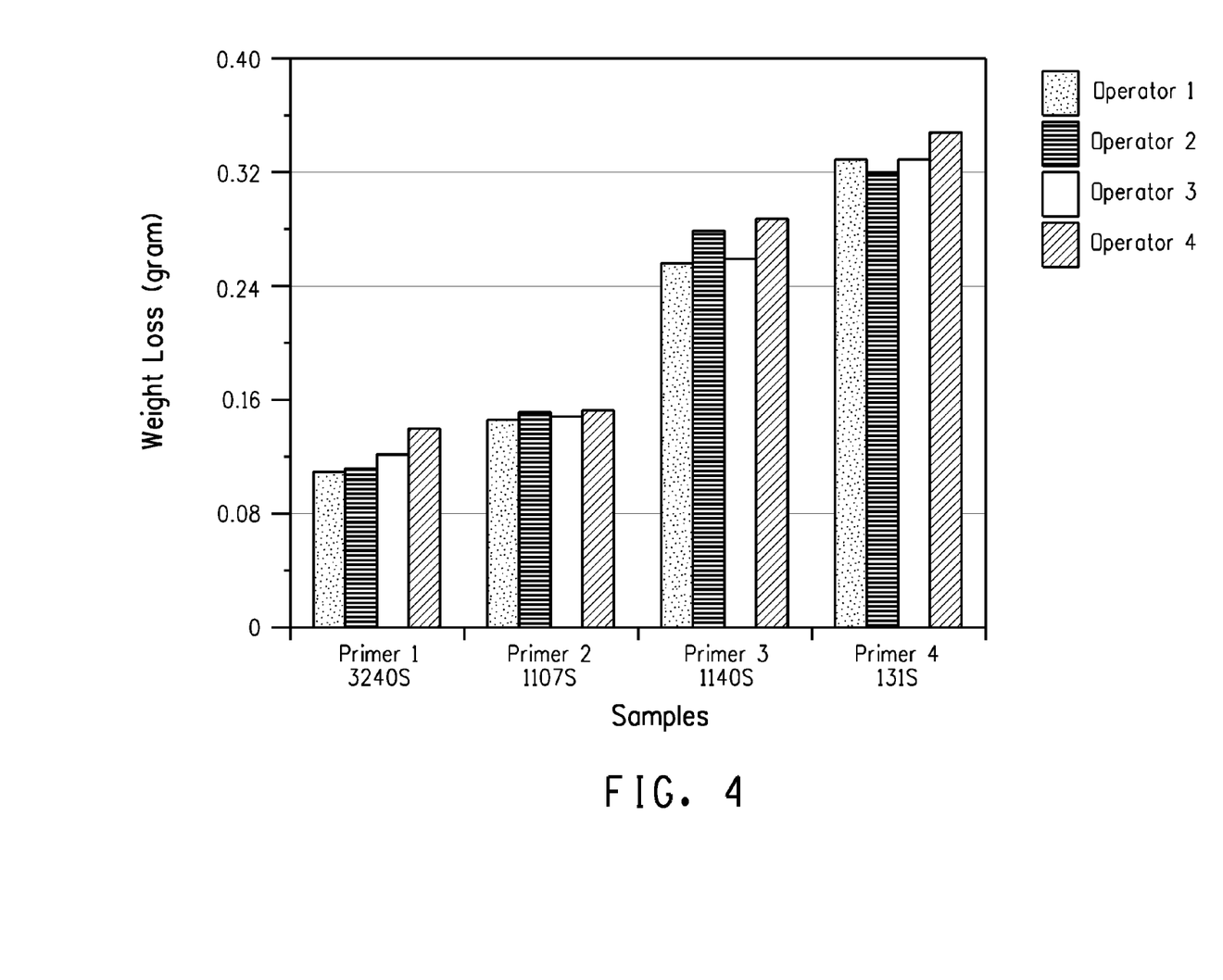
FIG. 4 shows examples of quantitative sanding results using the method of this invention.

Based on the sandability data, Primer 1 (3240S) had smallest weight loss under the given sanding conditions and was the most difficult to be sanded among the four primers tested. Primer 4 (131S) had the greatest weight loss and was the easiest among the 4 primers tested. Numerical values can also be associated to the primers to indicate individual sandability, such as "3" for primer 1, "5" for primer 2 (1107S), "6" for primer 3 (1140S) and "8" for primer 4.

Example 2

Buffing of Coatings

A testing panel coated with a clearcoat 7600S, available from DuPont, Wilmington, Del., was sanded for 8 cycles using the sanding device shown in FIG. 2. The panel was then buffed using 2000 RPM buffing rotor speed, with buffing compound Perfect-It III, available from 3M, St. Paul, Minn. 55144. Buffing time was selected between 6 seconds to 120 seconds.

Figure 5A:
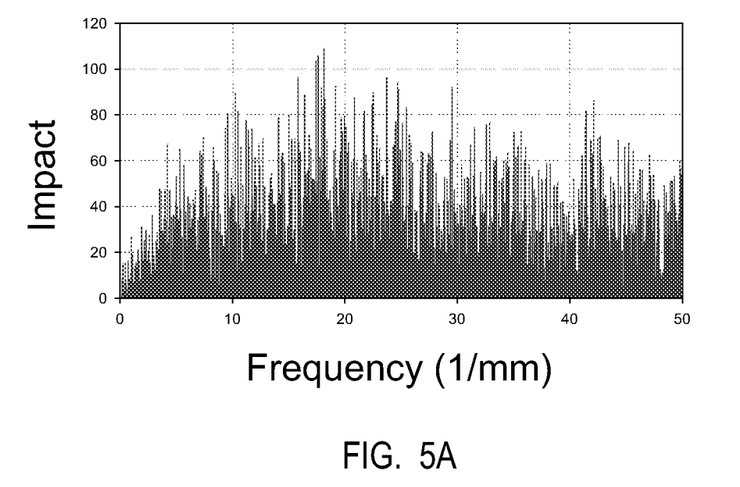
FIG. 5 shows representative buffing results.
Figure 5B:
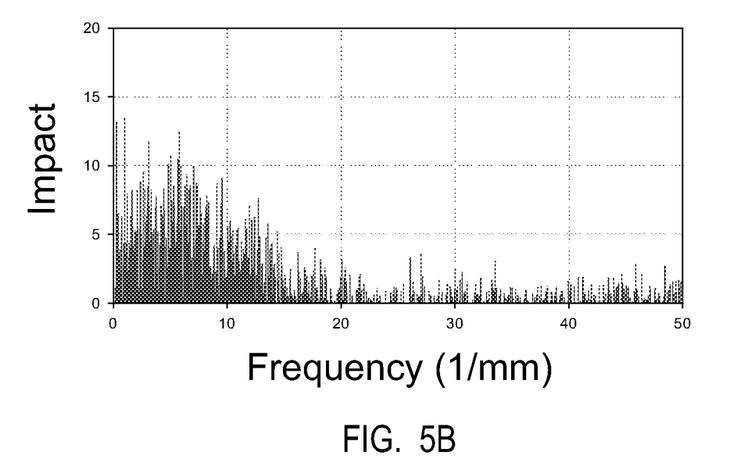
Figure 5C:
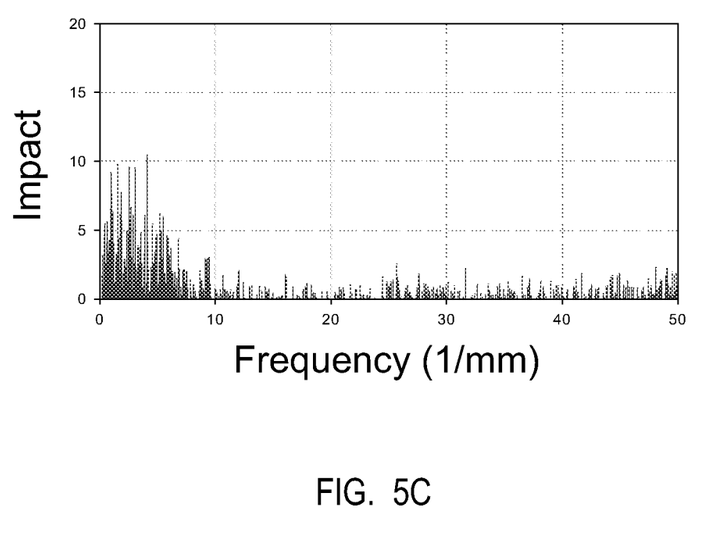

Profilometer measurements are shown in FIG. 5. The profilometer used was nano-scratch tester from CSM Instruments Inc. (Needham, Mass., USA). The profilometer measured heights of microstructures, shown as "impact" data in FIG. 5, on the clearcoat surface that were mostly microscopic lines caused by sanding and also the number of lines per millimeter, shown as "frequency" data in FIG. 5. Buffing is mostly effective in reducing heights of microstructures at high frequency. FIG. 5A shows profilometer measurement of the clearcoat after sanding, but before buffing. After 6 seconds buffing (FIG. 5B), most of high frequency microstructures were reduced in heights. After 48 second buffing (FIG. 5C), a further reduction in heights were achieved.

Example 3

Comparing Buffability of Coatings

Two clearcoats are sanded and buffed under same sanding and buffing conditions as described in Example 2. Profilometer measurements are obtained for both clearcoats. Both clearcoats have similar "impact" data indicating similar height and frequency of surface microstructures before buffing. After 6 second buffing, a first of the two clearcoat shows more than 80% reduction in heights while a second of the two clearcoat only has about 20% reduction in heights.

It is concluded that the first clearcoat has a buffability as "easy to buff" while the second clearcoat is more difficult to buff.

What is claimed is:

1. A method for measuring sandability of a coating, said method comprising the steps of:
    a) measuring initial characteristics of a substrate coated with said coating;
    b) sanding said coating on the substrate;
    c) measuring subsequent characteristics of the substrate after the step b); and
    d) obtaining a difference between the initial and the subsequent characteristics;
    wherein said substrate is sanded for a predetermined number of bi-directional sanding strokes by using a movement control device that is configured to provide said pre-determined number of bi-directional sanding strokes.

2. The method of claim 1 further comprising the step of repeating the steps b) through d).

3. The method of claim 1, wherein the initial characteristics of the substrate comprise an initial weight of the substrate and the subsequent characteristics of the substrate comprise a subsequent weight of the substrate.

4. The method of claim 1, wherein the initial characteristics of the substrate comprise an initial thickness of the coating on the substrate and the subsequent characteristics of the substrate comprise a subsequent thickness of the coating on the substrate.

5. The method of claim 1, wherein the initial characteristics of the substrate comprise initial roughness data of the coating on the substrate and the subsequent characteristics of the substrate comprise subsequent roughness data of the coating on the substrate.

6. A system for measuring sandability of a coating, said system comprising:
    a) a sanding device; and
    b) an substrate measuring device;
    wherein the sanding device comprises:
        i) a sanding head assembly;
        ii) a substrate holder that holds a substrate coated with said coating; and
        iii) an movement control device that causes relative movement between the substrate holder and the sanding head assembly; and
    wherein said movement control device is configured to provide a predetermined number of bi-directional sanding strokes.

7. The system of claim 6, wherein the sanding head assembly further comprises a sanding force regulator.

8. The system of claim 6, wherein the substrate measuring device is selected from a balance, a gloss meter, an imaging device, a proliformeter, or a combination thereof.

9. The system of claim 8, wherein the balance is capable of measuring weight differences in a range of from 0.0001 gram to 1 gram.

10. The system of claim 6 further comprising a buffing device and a surface measuring device.

11. A method for measuring sandability of an article, said method comprising the steps of:
  a) measuring initial characteristics of the article;
  b) sanding the article;
  c) measuring subsequent characteristics of the article after the step b); and
  d) obtaining a difference between the initial and the subsequent characteristics; wherein said article is sanded for a predetermined number of bi-directional sanding strokes by using a movement control device that is configured to provide said pre-determined number of bi-directional sanding strokes.

* * * * *